United States Patent [19]

Cornelis

[11] 4,365,509
[45] Dec. 28, 1982

[54] SYSTEM AND METHOD FOR DETERMINING THE WELL LOAD OF A HOPPER SUCTION DREDGE

[75] Inventor: Christiaan A. Cornelis, Papendrecht, Netherlands

[73] Assignee: IHC Holland N.V., Papendrecht, Netherlands

[21] Appl. No.: 235,557

[22] Filed: Feb. 18, 1981

[30] Foreign Application Priority Data

Feb. 20, 1980 [NL] Netherlands .................... 8001034

[51] Int. Cl.³ ............................................. G01F 23/00
[52] U.S. Cl. ................................. 73/290 V; 73/61 R; 73/290 R; 73/438
[58] Field of Search ...................... 73/61, 61.1, 290 R, 73/290 V, 438, 439; 33/126.6

[56] References Cited

U.S. PATENT DOCUMENTS

| | | |
|---|---|---|
| 2,779,045 | 1/1957 | Harvey . |
| 3,344,659 | 10/1967 | Chambers .................... 73/61.1 R |
| 3,543,565 | 12/1970 | Konig et al. .................... 73/61 R |
| 3,628,263 | 12/1971 | van der Veen .................... 73/438 |
| 3,690,180 | 9/1972 | van der Veer .................... 73/438 |
| 3,757,813 | 9/1973 | Levenberg . |
| 3,922,921 | 12/1975 | Woo .................... 73/432 |
| 3,935,741 | 2/1976 | Zinsmeyer .................... 33/126.6 |
| 4,162,473 | 7/1979 | Utasi .................... 73/290 V |

FOREIGN PATENT DOCUMENTS 564537 7/1977 U.S.S.R. .................... 73/61 R

*Primary Examiner*—S. Clement Swisher
*Attorney, Agent, or Firm*—Young & Thompson

[57] ABSTRACT

A method and apparatus for measuring the amount of mire and mud in a suction dredge hopper 2, which mire and mud is a constituent of a fluidized mixture. An acoustic level gauge 16 measured the position of the upper surface 3 of the mixture and a plumb weight 7 measures the position of the lower limit of the mixture defined by the top of a sand layer 4. A plurality of differential pressure responsive density measuring devices P measure the density of mire at different levels. From these measured valves the total amount of mud and mire is determined.

11 Claims, 4 Drawing Figures

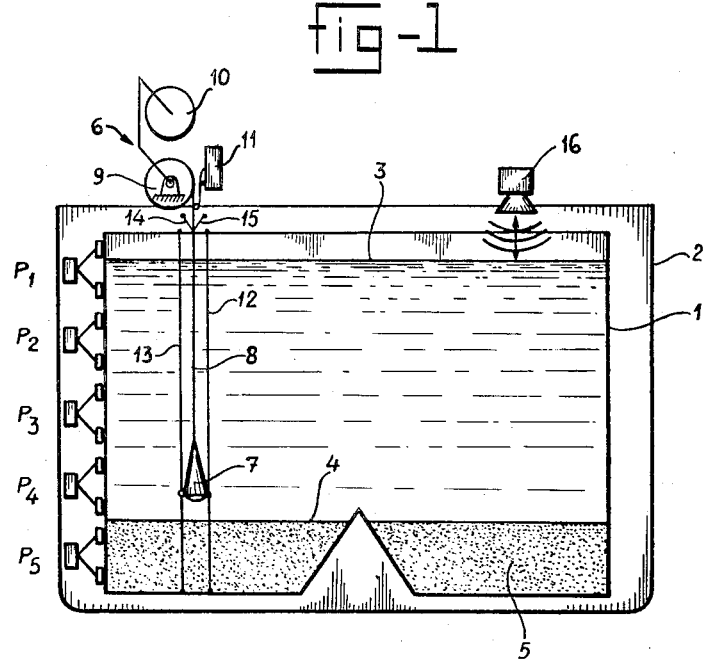
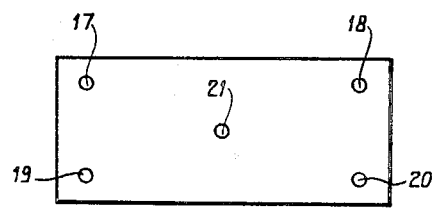
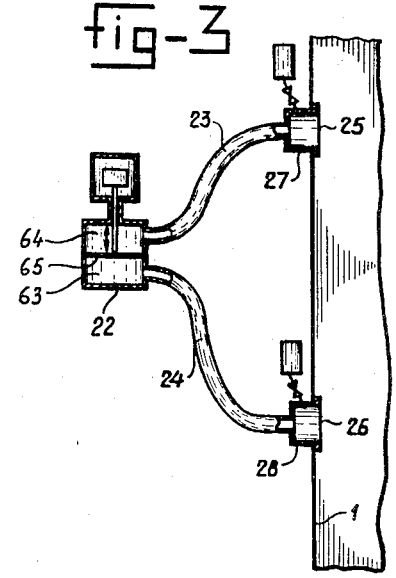

SYSTEM AND METHOD FOR DETERMINING THE WELL LOAD OF A HOPPER SUCTION DREDGE

The invention relates to a system and method for determining the well load of a hopper suction dredge, especially for determining the total amount of dredged mixture, consisting of a settled mixture and mire and mud, contained as a fluidized mixture together with dredged water in the well of a hopper suction dredge.

In many river entrances, harbours and at the outside thereof connecting waterways the deposit of mire, for instance caused by sediment transport in rivers may create in the long run serious obstacles for ships with considerably draught, such as oil tankers. Even if the top layer of the sandy bottom is at sufficient depth or is dredged to a sufficient depth, it is possible that over a longer period mire and mud are settling thereon in the form of a permanent mire layer, so that the allowed draught will decrease again It will be clear that this is undesirable and therefore in the above mentioned areas continuously dredging operations are carried out to remove said mire layer by order of the government or the harbour authorities.

During this kind of dredging operations one is aiming at removing the mire and mud layer, however leaving the sandy bottom mainly untouched. Said sandy bottom is already at a sufficient depth. It is therefore important for the principals and for the dredging companies to know how much mire and mud is removed and with how much sand on board a fully loaded hopper dredge is returning.

For determining the amount of mire in the dredged mixture already several methods and systems are known. According to one known method examples of the dredged mixture are taken at regular intervals and on the bases of these samples the amount of mire and mud is determined. According to another known method the specific weight of the flowing spoil is continuously measured into the suction pipes. Because the specific weight of sand with an apparent volume concentration of 40% is approximately, 1,4 and the specific weight of mire with a concentration of 5% is approximately 1,15 it is possible to make a rough estimation of the division in the dredged mixture in the well of the hopper suction dredge. Furthermore a method is known according to which through a number of pipes, vertically positioned above each other and opening into the well, water may be pumped into the well and the counter pressure is measured to determine the height of the upper sand layer and the level of the total load. In this case pressure gauges could be used, measuring the total pressure at the lowest level in the well.

An object of the invention is to supply another system and method of the type mentioned in the first paragraph, by means of which the amount of mire and mud in the load of a hopper section dredge may be determined in a more precise way. Also the amount of dredged sand may be measured and if necessary the system may be used for equable loading the hopper suction dredge.

According to a characteristic of the invention means are present for measuring the upper level of the total load in the well of a hopper suction dredge at one or more suitable positions using a sounder; means for measuring the upper level of the settled material onto one or more suitable positions using a plumb; means for determining the specific weight of the mire in the fluidized mixture in the area between the upper level of the total load and the upper level of the settled material; means for determining the total amount of mire in the fluidized mixture based on the above mentioned data and on the further dimensions of the well.

For determining the specific weight of the mire in the fluidized mixture preferably differential pressure gauges are used for measuring pressure differences in the fluidized mixture between two points in the well positioned at a known vertical distance of each other.

For measuring the pressure difference it is possible to use two separate pressure gauges, positioned at different vertical levels, which pressure gauges are for instance converting an hydraulic pressure signal into a analog electrical pressure signal. The pressure difference may be determined by subtracting said electrical signals. Thereafter, for determining the specific weight, it is necessary to compensate for the water in which the mire is fluidized, because said water also aids to the pressure difference in the two measuring points. Such a compensation could be effected by using electrical means.

A simple and more effective compensation however is realized by using a differential pressure gauge which is through conduit pipes connected to the pressure measuring points, positioned at the vertical distance of each other. In the pressure measuring points these conduit pipes are closed and filled with water, such that no fluidized mixture is able to penetrate. Therefore in the differential pressure gauge itself there is no water pressure difference, but only a pressure difference caused by the mire and mud fluidized in the water in the well.

Because the specific weight of the fluidized material will in general vary with the height in the well preferably a number, for instance five, differential pressure gauges are installed above each other, whereby one could either use an average value of the data from all said pressure gauges for determining the specific weight of the tatal load, or one could subdivide the well in the horizontal direction in sectors belonging each to a differential pressure gauge, each of which the total amount of mire can be determined. Said last mentioned measurement is preferred if the mire is unequally divided in vertical direction.

The above mentioned differential pressure gauges are preferably installed into a hollow post which may be vertically lowered into the middle of the well and if necessary removed. Differential pressure gauges which are partially or totally enclosed by the settled material such as sand, or are partly or totally above the highest load level, will indicate such a high respectively low pressure difference that amongst others therefore they could be easily switched electrically out of the measuring circuit.

The momentaneous upper level of the total load in the well is preferably determined using one or more acoustical sounders with an acoustical converter, which is installed above the maximum load level and is generating acoustical waves downwards. The load level is calculated in a known way out of the time difference between the moment of transmitting each acoustical pulse and the moment of receiving the corresponding reflected pulse. Of course also acoustical pulses will be reflected by the top layer of the settled material, but because the transition between the fluidized mixture and the settled material such as sand will not be sharp said reflected pulse will be relatively weak and furthermore will differ in shape from the pulse reflected by the upper surface of the total load, such, that it is very easy to electrically discriminate the desired stronger pulses from the weaker pulses. The settled material causes such an attenuation, that pulses reflected by the ship's bottom cannot have any disadvantageous influence on the measurement.

With a low level at the start of the dredging operations there will be no or less settled material such as sand on the bottom of the well, so that also said bottom is able to reflect stronger pulses. Of course the same phenomenum will set in when only mire, fluidized in the water, is dredged, however, because the pulses reflected by the bottom are received later than the pulses reflected by the upper water surface, said delayed pulses from the bottom can be locked using electrical distance gates. If at the start of the dredging operations the water level in the well is still low and there is no sand on the bottom then the measurements of the amount of mire in the fluidized mixture are of less importance.

According to the invention the upper level of the settled material is preferably measured by means of one or more mechanical automatic plumbs. Said devices comprise a weight with a known fixed length, a measuring tape or line carrying said weight and a winch for lowering said weight onto the settled material and for hoisting said weight. Using for instance a counter the length of the produced tape or line may be measured, whereby the fixed length of the weight is added. Also a direct measurement of the produced tape or line is possible.

The total weight of that part of the dredged load, in which only fluidized material is floating, may be determined by mutually comparing the highest level measured with the acoustical converter and the depth of the settled material level measured with the mechanical plumb. The moment at which the weight arrives the upper surface of the settled material can be determined by means of a device reacting onto the line or tape tension, for instance a spring biased cam, pressed against the line and used for operating an electrical switch.

As will be clear from the above mentioned an acoustical measurement of the upper layer of the settled material will be hindered by the non sharp transition. If one would use an upwards generating acoustical converter onto the bottom of the well, one also would encounter said problems and one may expect much hindrance because of strong pulses reflected by the upper water surface.

Hereafter the invention will be explained referring to the embodiments illustrated in the figures.

FIG. 1 shows a schematical sectional view of the well of a hopper suction dredge, in which the measures according to the unterlining application are brought into practice;

FIG. 2 shows a schematical top view of the well of a hopper suction dredge with the position of the various gauges;

FIG. 3 shows a side view of a differential pressure gauge used in the system and the method according to the present invention;

FIG. 1 shows schematically a sectional view of a well 1 of a hopper section dredge having an outer ship's wall 2.

Figure 4:
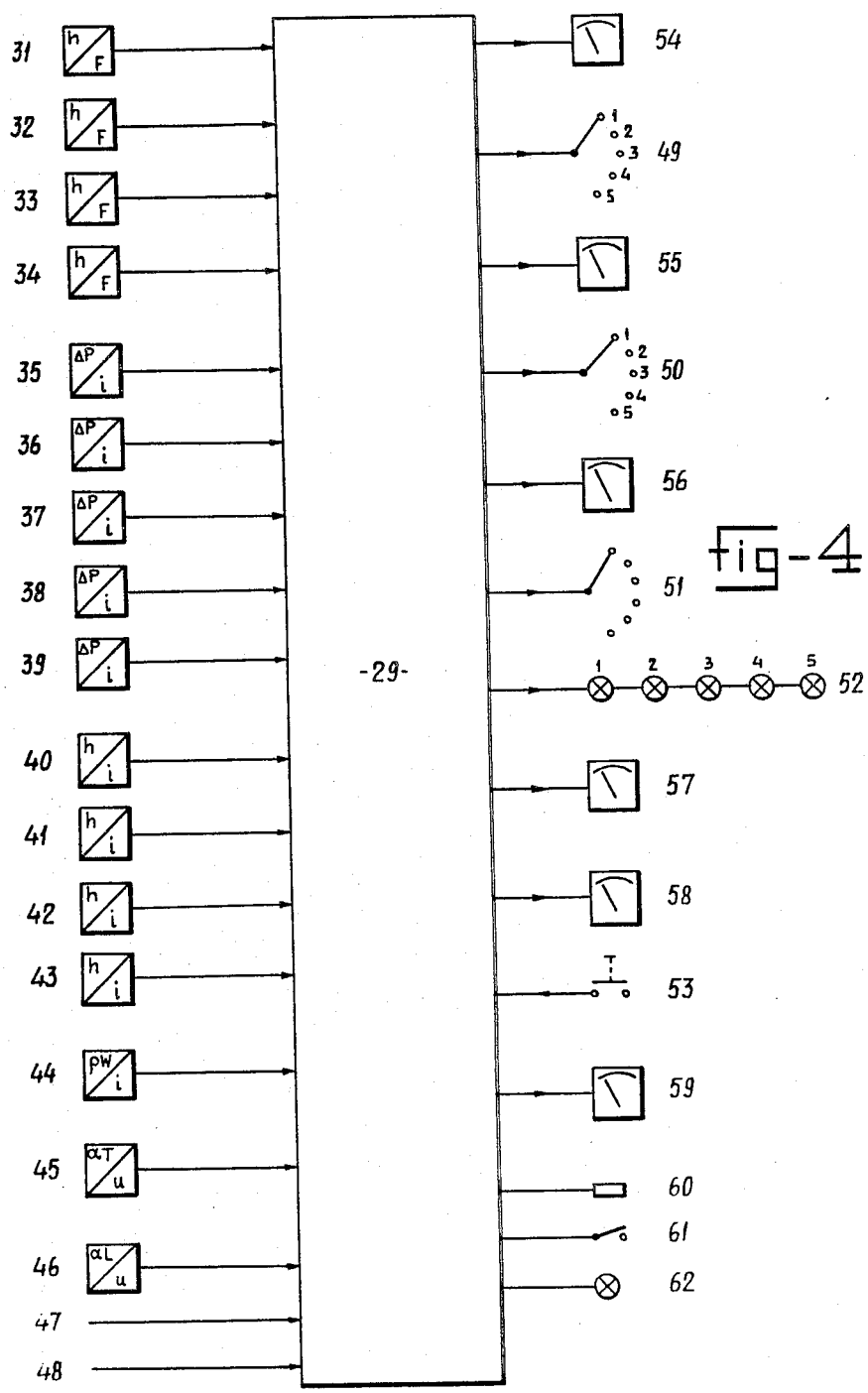
FIG. 4 shows a block diagram of the processor unit for the electrical signals supplied by the measuring devices according to the present invention.

Said well 1 is between the transition layer 4 indicating the momentaneous level of the settled solid material, mainly consisting of dredged sand 5, and the highest load level 3, filled with spoil, mainly consisting of a fluidized mixture of water, mire and mud. As a matter of course the upper layer 4 will not necesarily show a sharp transition as is denoted by the sharp line in the figure.

The reference number 6 is used for the schematically illustrated mechanical plumb gauge used for determining the upper level 4 of the settled material 5. Said plumb gauge 6 contains a plumb 7, connected to a steel measuring tape 8. Said measuring tape 8 and the weight 7 can be lowered or hoisted by means of a tape reel 9, coupled to an electrical drive motor. A counter 10 is mechanically coupled to the shaft of said tape reel 9 or to the electric motor and is used for instance to convert the number of revolutions of said shaft into length units of the measuring tape 8, taking into account the diameter of the measuring tape wounded onto said tape reel. The level 4 of the settled material is determined by means of the length of the produced measuring tape 8 increased by the length of the weight 7. If the weight 7 is in its upmost position, then the counter 10 is reset to zero. Thereafter the weight 7 is lowered until it reaches the upper layer 4. The underside of said weight is suitably formed, for instance rounded, such that it will sink into settled material until an expected depth. Thereby the tension in the measuring line will disappear, which will be detected using a tension detector 11. This detector may consist of a switch, for instance switching off when the measuring tape is tightly stretched, and switching on when the weight touches the upper layer 4, whereby the tape slackens and the counter pressure against a switch spring disappears. It is of course possible to use other detection means.

During the lowering of the weight 7 the produced length of the measuring tape 8 is counted until the weight 7 touches the sand layer 5. To determine the upper level 4 of said sand layer periodically the weight is repeatedly hoisted over a small distance for instance 50 cm above said upper level and is thereafter lowered until it reaches the sand layer. By hoisting to only 50 cm above the level it is possible to use a higher measuring frequency than would be possible in case the weight is hoisted up unto the reel 9. In this way it is possible to carry out a level measurement of level 4 each 5 à 10 sec.

To prevent swinging of the weight 7 because of ship movements resulting into none accurate measurements, the weight can be attached vertically movable between two tightly stretched steel wires 12, 13. At the upper side below the tape tension converter 11 a wiper is positioned, for instance comprising two spring tensioned wiper knives 14 and 15 pressed against the tape 8. Said knives wipe mud and mire of the tape 8, so that the measurement is not disadvantageously influenced and also the reel 9 is not polluted. The mud and mire sticking to the tape 8 may be received in an easy to clean mire compartment. The reel motor should have a couple limiter functioning in case the weight 7 is sticking into the sand or is otherwise blocked.

The total load level, that means the highest level 3 in the well is determined in the system and the method according to the present invention using an acoustical gauge 16. This acoustical gauge may comprise a converter converting electrical pulses into acoustical pulses and reconverting the received acoustical pulses after reflection against the transition layer 3 again into electrical signals. The distance between the converter 16 and the level 3 can be derived out of the time difference between the transmitted pulses and the received reflected pulses. As is already above mentioned reflections caused by the level 4 and by the ship's bottom may easily blocked.

The acoustical gauge 16 is attached at a predetermined position above the hopper space, preferably close to the device for determining the sand level 4 that means the reel 9 and the devices 10 and 11.

The level 4 of the sand layer as well as the maximum load level 3 are determined in an embodiment of the invention by means of the above described mechanical and acoustical measuring devices at four positions in the well as is indicated in FIG. 2 with the reference numbers 17 until 20. Level differences caused by movements of the mire and ship movements can be averaged in this way.

For measuring the specific weight of the mire which is in fluidized condition between the levels 3 and 4, five differential pressure gauges $P_1$ until $P_5$ are used. In the figures said gauges are for the sake of clearness illustrated attached to a vertical wall of the well. In practice however said gauges will be positioned into a hollow post, which will be lowered approximately in the middle of the well, at 21 in FIG. 2, until it vertically extends to the bottom of the well and may be removed if necessary.

Each differential pressure gauge $P_1$–$P_5$ in the herein described embodiment comprises a converter 22 (FIG. 3) determining a pressure difference between two pressure measuring points in the well. The two pressures acting in said points could be transmitted through hydraulic conduit pipes to two pressure chambers 63,64 at both sides of a diaphragm 65 or another pressure sensitive element in the converter 22. The deflections of said diaphragm 65 are related to the pressure difference. Said pressure difference is converted into a corresponding electrical signal. Each pressure chamber is connected to a hydraulic conduit pipe 23, 24, leading to the well 1 through membranes 25, 26 closing the chambers 27 respectively 28. Said two chambers 27, 28 are vertically above each other attached at a predetermined distance of each other, for instance 1 m. The chambers 25, 26, the conduit pipe 23, 24 and the not illustrated chambers in the differential pressure gauge 22 are filled with liquid for instance water, with a known specific weight, which specific weight is preferably equal to the specific weight of the water in the well without the therein floating solid particles of mire and mud. Of course provisions should be made for easily filling the chambers and the conduit pipe with the desired liquid and for deaerating if necessary.

By using two pressure measuring points at a known mutual vertical distance of each other and by measuring the pressure difference with compensation of the water pressure as above mentioned the presure difference in the differential pressure gauge 22 over the distance between the pressure measuring points, caused by the water in the well, is compensated and only the specific weight $p$ of the solid particles floating into the water is measured by the differential pressure gauge. Said specific weight in the volume section between the two chambers 27 and 28 can be found by dividing the real pressure differences determined in the differential pressure gauge by the distance between the two chambers 27 and 28. The total mass of the solid particles floating in the water in this section is determined by multiplying the resulting specific weight with the volume of the section between the levels of the measuring chambers 27 and 28.

Because the density of the floating material and therefore also the specific weight may vary over the total height of the well preferably measurements are carried out in a number of sections in vertical direction, in the illustrated embodiment in five sections. The volume of these sections are determined from the relation with the filling level through the known characteristic form of the hopper. Also the fact that one or more pressure gauges are not active because the related measuring points, that means the membranes 25 and 26 are not or not longer in contact with the fluidized mixture, will be taken into account. It is for instance possible that the pressure measuring points of the lowest differential pressure gauge, for instance $P_5$ are after some time partly or totally covered by the settled material 4, whereas the pressure measuring points of the uppermost pressure gauge, for instance $P_1$ are at the start not necessarily below.the highest load level 3. the same applies of course to one or more of the pressure gauges $P_2$, $P_3$ and $P_4$. In both above mentioned situations the differential pressure gauges $P_1$ and $P_5$ are not able to supply reliable measuring signals. The indicated pressure differences will have a value which is in relation to the expected value too low or too high, and the converted electrical signals thereof could be used for switching off these not sufficiently active differential pressure gauges. Also the signals from the level detectors 6 and 16 could be used for switching off the not usable differential pressure gauges.

The signals, supplied by the active differential pressure gauges $P_2$, $P_3$ and $P_4$ are representative for the specific weight in the sector, belonging to each of said gauges. If the mire floating into the water is relatively homogeneous divided over the well height, then only one pressure difference measurement carried out by the lowest active differential pressure gauge is sufficient. It is clear that the salt contents of the water in the well, the trim and the list should be taken into acount when the specific weight is determined. The salt contents could be determined for instance by measuring the electrical conductivity of the water.

FIG. 4 shows schematically the electrical processing unit 29, to which at the left side the signals are supplied generated by the various above described measuring devices. To start with this are the signals related to the height of the levels 3 and 4 delivered by the level gauges and supplied to the inputs 31–34 respectively 40–43. Furthermore there are the signals concerning the specific weight delivered by the differential pressure gauges $P_1$–$P_5$, which are supplied to the inputs 35–39.

The measuring devices for measuring the sand level 4 are converting the measured level into a pulse series with a height dependent pulse frequency.

The measuring devices for the upper level 3 are converting the measured level into an electrical current the amplitude of which varies level dependent between 4 and 20 mA.

The levels 3 and 4 are measured at four different positions 17–20, that means at the front side as well as at the back side, at the port side and at the starboard side. The processing unit 29 derives an average value out of the four delivered values. Because the measurements are electrically processed the corresponding calculations could be carried out very fast such that each momentary determination approximately corresponds to the situation in which the ship is horizontal and not moving.

Also the differential pressure gauges $P_1$-$P_5$ are converting the pressure difference, which is exclusively related to the pressure caused by the solid particles, into a current with for instance a pressure dependent amplitude between 4 and 20 mA. As soon as the measured pressure causes a signal outside this current region then the concerned gauge is switched off by the processor 29.

The processor 29 furthermore receives signals concerning the salt contents at 44, concerning the trim between $+4°$ and $-4°$ at 45, concerning the list between $+8°$ and $-8°$ at 46 and concerning the activated state of the dredge pumps at 47. The power supply is connected at 48.

The processor 29 is connected to a number of switches 49, 50 and 51 for switching on each of the gauges for measuring the sand level, the water level and the specific weight each separately or all simultaneously and for measuring the specific weight also the gauges which are buried in the mire, that means below the level 4. If all the gauges are switched on simultaneously then the average from all the measurements is taken. The signal lamps at 52 are indicating which of the differential pressure gauges $P_1$ and $P_5$ are participating in the measurement. Furthermore there is a push button 53 for initiating between times the counters 10 of the devices for measuring the sand level 4. If none of the dredge pumps is operating, then said sand level gauges are automatically moved to their reference positions after which the counters are initiated.

Based on the results of the measurements the processing unit 29 delivers at the right side in FIG. 4 by means of suitable indication devices the following data, corrected for trim, list and salt contents: the height of the sand level 4 in a meter at 54, the height of the water level 3 in a meter at 55, the specific weight of the fluidized mixture in tons per m³ at 56, the total mass of the settled solid material in tons at 57, the total mass of the fluidized solid particles in tons at 58 and the loading speed in tons per second at 59.

The special advantage of the system according to the present invention is that by means of this system it is for the first time possible to measure momentaneously and simultaneously the total mass of the settled solid material as well as the total mass of the fluidized solid particles. For that purpose the meters 57 and 58 in FIG. 4 are used.

It will be clear that also registering devices could be used in stead of this indication devices, so that a change in the various signals in relation to time will be made visible. The reference symbols 61 and 62 are indicating for instance a fuse, a power switch, respectively a signal lamp indicating the "on" or "off" condition. The processing unit 29 may comprise a suitable microprocessor with memory means, programmed especially for measuring the well load.

It will be clear that the invention is not restricted to the above described and illustrated system and the parts thereof but that amendments and changes are possible within the scope of the invention.

I claim:

1. Well measuring system for a hopper suction dredge, especially for determining the dredged total amount of mixture consisting of a settled mixture and of mire and mud contained as a fluidized mixture into the dredged water in the well of a hopper suction dredge, characterized by means for measuring the upper level of the total load at one or more positions in the well of the hopper suction dredge using a sounder device; means for measuring the upper level of the settled material at one or more suitable positions using a plumb device; means for determining the specific weight of the mire in the fluidized mixture in the area between the upper level of the total load and the upper level of the settled material; means for determining the total amount of mire in the fluidized mire mixture based on the above mentioned data and on the other dimensions of the well.

2. Well measuring system according to claim 1, characterized in that the means for determining the specific weight of the fluidized mixture comprise one or more differential pressure gauges measuring pressure differences in the fluidized mixture between two points in the well with known vertical distance to each other.

3. Well measuring system according to claim 2, characterized in that a number of differential pressure gauges is installed along side each other in the well in a uniformly divided vertical row from the bottom until the highest possible load level, and that means are present to determine an average value for the specific weight based on the measurements of said number of differential pressure gauges.

4. Well measuring system according to claim 2 characterized in that each differential pressure gauge is by means of conduit pipes connected to two corresponding pressure measuring points vertically positioned at a known distance of each other, which conduit pipes are filled with liquid with known specific weight, preferably equal to the specific weight of water, and which conduit pipes are closed at the measuring points by means of elastic membranes, the outside of which is exposed to the pressure of the load in the well.

5. Well measuring system according to claim 3 or 4 characterized in that the differential pressure gauges are installed into a removable hollow post, which is positioned approximately in the center of the well.

6. Well measuring system according to claim 1, characterized in that the means for measuring the upper level of the settled material comprise at least one depth measuring device having hoisting and lowering means for a plumb suspended at a measuring cable, counting means for counting the distance, traveled by the weight during lowering and hoisting and means for determining the fact that the weight touches the upper level of the settled material by measuring the tension in the measuring cable.

7. Well measuring system according to claim 1, characterized in that the means for measuring the maximum load level comprise at least one acoustical distance measuring device, mounted above the highest possible load level in the well.

8. Well measuring system according to claim 1, characterized in that means are present for switching off those differential pressure gauges which are above the momentaneous total load level or below the momentaneous settled material level.

9. Method for determining the well load in a hopper suction dredge, especially for determining the dredged amount of mire, which is contained in the well of the hopper suction dredge as a fluidized mixture, characterized in that the maximum load level is measured at least at one point in the well; the upper level of the settled material is measured at least at one point in the well; the specific weight of the fluidized mire mixture in the area between the maximum load level and the upper level of the settled material is determined; the total amount of mire in the fluidized mire mixture is determined based on the resulting data and on the known well dimensions.

10. Method according to claim 9, characterized in that the specific weight of the fluidized mire mixture is determined at least at one point by means of the pressure difference measured at two points vertically above each other with known mutual distance.

11. Method according to claim 9, characterized in that the maximum load level is determined using acoustical means and the upper level of the settled material is determined using mechanical means.

* * * * *